United States Patent [19]
Ralston et al.

[11] Patent Number: 6,066,450
[45] Date of Patent: May 23, 2000

[54] DIAGNOSTIC AND THERAPEUTIC METHODS AND APPARATUS BASED ON INTERLEUKIN-6 GENE POLYMORPHISMS

[75] Inventors: Stuart Hamilton Ralston, Aberdeen, United Kingdom; Struan Frederick Airth Grant, Sydney, Australia

[73] Assignee: Gemini International Holdings Limited, Monaco

[21] Appl. No.: 08/857,464

[22] Filed: May 16, 1997

[30] Foreign Application Priority Data

May 16, 1996 [GB] United Kingdom ............... 9610281

[51] Int. Cl.$^7$ .................................... C12Q 1/68
[52] U.S. Cl. .................................... 435/6; 514/2
[58] Field of Search ................. 435/6, 91.2; 536/24.33, 536/24.31; 935/77, 78; 424/130.1; 514/2

[56] References Cited

U.S. PATENT DOCUMENTS

| | | | |
|---|---|---|---|
| 5,402,781 | 4/1995 | Dimarogonas | 128/653.1 |
| 5,436,258 | 7/1995 | Blake et al. | 514/372 |
| 5,440,012 | 8/1995 | Takei et al. | 530/307 |
| 5,441,964 | 8/1995 | Bryant et al. | 514/324 |
| 5,593,833 | 1/1997 | Morrison et al. | 435/6 |

FOREIGN PATENT DOCUMENTS

| | | |
|---|---|---|
| 0 331 640 | 9/1989 | European Pat. Off. . |
| 9-12592 | 1/1997 | Japan . |
| 9-25293 | 1/1997 | Japan . |
| 9-30977 | 2/1997 | Japan . |
| WO 97/03060 | 1/1997 | WIPO . |
| WO 97/04799 | 2/1997 | WIPO . |
| WO 97/06254 | 2/1997 | WIPO . |

OTHER PUBLICATIONS

Bowcock, A.M., et al., "Rapid detection and sequencing of alleles in the 3' flanking region of the interleukin–6 gene," *Nucl. Acids Res.* 17(17):6855–6864 (1989).

Fugger, L., et al., "IL–6 Gene Polymorphism in Rheumatoid Arthritis, Pauciarticular Juvenile Rheumatoid Arthritis, Systemic Lupus Erythematosus, and in Healthy Danes," *J. Immunogenet.* 16:461–465 (1990).

Jacob, C.O., et al., "DNA polymorphism in cytokine genes based on length variation in simple–sequence tandem repeats," *Immunogenetics* 38:251–257 (1993).

Linker–Israeli, M., et al., "A Greater Variability in the 3' Flanking Region of the IL–6 Gene in Patients with Systemic Lupus Erythematosus (SLE)," *Autoimmunity* 23:199–209 (Mar. 1996).

Linker–Israeli, M., et al., "Skewed Allele Distribution of the IL–6 Gene Associated Minisatellite in Patients with SLE," *Journal of Investigative Medicine* 44(3):276a (May 1996).

Morrison, N.A., et al., "Prediction of bone density from vitamin D receptor alleles," *Nature* 367:284–287 (1994).

Narayanan, S., "Laboratory Markers as an Index of Aging," *Am. Clin. Lab. Sci.* 26(1):50–59 (Jan.–Feb. 1996).

Radford–Smith, G., and Jewell, D.P., "Cytokines and inflammatory bowel disease," *Baillière's Clinical Gastroenterology* 10(1):151–164 (Mar. 1996).

English Language Abstract of Japanese Patent Publication No. 9–12592 (Document AM1), Derwent World Patents Index, WPI Accession No. 97–128739.

English Language Abstract of Japanese Patent Publication No. 9–25293 (Document AN1), Derwent World Patents Index, WPI Accession No. 97–149801, (Jan. 1997).

English Language Abstract of Japanese Patent Publication No. 9–30977 (Document AP1), Derwent World Patents Index, WPI Accession No. 97–161424, (Jan.–Feb. 1997).

International Search Report for International Application No. PCT/GB97/01337, (1997).

Murray et al. Bone (1997) 21(1):89–92.

*Primary Examiner*—Lisa B. Arthur
*Attorney, Agent, or Firm*—Sterne, Kessler, Goldstein & Fox PLLC

[57] ABSTRACT

The present invention provides methods of diagnosis of certain disease states, such as osteoporosis, that are associated with polymorphisms in an IL-6 gene, comprising determining the genotype of an IL-6 gene. The invention is also directed to methods of identifying an individual predisposed or susceptible to certain disease states, such as osteoporosis, associated with polymorphisms of an IL-6 gene, comprising determining the genotype of an IL-6 gene in the affected individual. The invention is further directed to compositions useful for determining the genotype of an IL-6 gene, to kits and diagnostic apparatuses comprising such compositions, and to methods of treatment of diseases associated with IL-6 genetic polymorphisms.

13 Claims, No Drawings

DIAGNOSTIC AND THERAPEUTIC METHODS AND APPARATUS BASED ON INTERLEUKIN-6 GENE POLYMORPHISMS

FIELD OF THE INVENTION

The present invention is in the fields of molecular and cellular biology. The invention generally relates to diagnostic methods and apparatus based upon a polymorphism in an interleukin-6 (IL-6) gene. More specifically, the invention relates to methods and apparatus for diagnosis and treatment of pre-disposition to certain disease states, by screening for the presence of an IL-6 genetic polymorphism, and more specifically to diagnosis and treatment of predisposition to osteoporosis.

BACKGROUND OF THE INVENTION

Methods and apparatus for determining bone density and diagnosing osteoporosis are known from U.S. Pat. No. 5,402,781. The methods and apparatus described therein, however, only enable diagnosis of this condition once it is well established and significant loss in bone density has occurred; they do not allow the identification of individuals who are predisposed or have an increased susceptibility to osteoporosis.

Hormone replacement therapy is an established treatment for osteoporosis and has proved successful in halting further decline in bone density that is characteristic in women suffering from this disease. Hormone replacement therapy is generally not, however, able to bring about a reversal of osteoporosis; that is, it is not capable of inducing an increase in the bone density of sufferers.

While osteoporosis is well-known as a condition affecting postmenopausal women, significant numbers of men are also affected by the disease. Each year approximately one third of hip fractures occur in men. Treatments for osteoporosis in men are available but tend only to delay or stop further bone density loss.

It would, accordingly, be of particular advantage to be able to identify with increased accuracy those individuals having a predisposition or increased susceptibility to osteoporosis. Suitable therapy could then be put into place before the effects of osteoporosis set in.

SUMMARY OF THE INVENTION

It is an object of this invention to provide method and apparatus for detecting individuals having a predisposition or susceptibility to certain disease states, in particular, osteoporosis. It is a further object of the invention to identify individuals having such a predisposition or susceptibility by determining a relevant genotype of an individual. It is another object of the invention to provide a therapy for those individuals have a predisposition or susceptibility to certain disease states. A still further object of the invention is to provide a therapy for those individuals having a predisposition or susceptibility to osteoporosis. Another object is to provide the use of means for determining a relevant genotype in manufacture of apparatus for diagnosis of predisposition or susceptibility to osteoporosis.

In one embodiment, the invention provides a method of diagnosis of a disease, preferably osteoporosis, in an animal (preferably a human) comprising determining the genotype of an IL-6 gene in the animal. The invention is also directed to a method of identifying an animal (preferably a human) predisposed or susceptible to a disease, preferably osteoporosis, comprising determining the genotype of an IL-6 gene in the animal. Such methods preferably comprise determining whether the animal is homozygous or heterozygous for polymorphisms of the IL-6 gene. Such determinations may be accomplished by screening the 3' flanking region of the IL-6 gene in an animal to identify a polymorphism in the 3' flanking region of the IL-6 gene. Polymorphisms identified according to these methods are indicative of a risk genotype, which is preferably a homozygous IL-6 genotype or a heterozygous IL-6 genotype wherein the nucleic acid sequence is not 675 base pairs in size and is not 695 base pairs in size. This screening may be accomplished by a technique selected from the group of techniques consisting of amplification of a nucleic acid sequence located within the 3' flanking region of the IL-6 gene, Southern blotting of the 3' flanking region of the IL-6 gene and single strand conformational polymorphism (SSCP) mapping of the 3' flanking region of the IL-6 gene, and is most preferably accomplished by amplification of a nucleic acid sequence located within the 3' flanking region of the IL-6 gene. According to the invention, the amplification is preferably accomplished by the polymerase chain reaction using one or more primers adapted to amplify a nucleic acid sequence located within said 3' flanking region of the IL-6 gene. Preferred primers used in such amplification have a nucleotide sequence selected from the group of nucleotide sequences consisting of SEQ ID NO: 3 and SEQ ID NO: 4. According to the invention, the nucleic acid sequence located within the 3' flanking region of the IL-6 gene is located between a restriction site recognized by HindIII or an isoschizomer thereof and a restriction site recognized by RsaI or an isoschizomer thereof, and the polymorphism is located in a TA repeat sequence within said 3 flanking region of the IL-6 gene. Polymorphisms identified according to these methods preferably have a nucleotide sequence selected from the group of nucleotide sequences consisting of SEQ ID NO: 1 and SEQ ID NO: 2.

The invention is also directed to an isolated nucleic acid molecule having a nucleic acid sequence as set forth in SEQ ID NO: 3 or SEQ ID NO: 4.

The invention is also directed to compositions for use in diagnosing a disease (preferably osteoporosis) in an animal, or for use in identifying an animal predisposed or susceptible to a disease (preferably osteoporosis), comprising one or more primer nucleic acid molecules adapted to amplify a portion of a 3' flanking region of an IL-6 gene in the animal (preferably a human). The primer nucleic acid molecules according to this aspect of the invention are preferably capable of identifying a polymorphism in the 3' flanking region of the IL-6 gene, the polymorphism being indicative of a risk genotype in said animal. The polymorphism is preferably located in a TA repeat sequence within the 3' flanking region of an IL-6 gene in the animal, and most preferably has a nucleotide sequence selected from the group of nucleotide sequences consisting of SEQ ID NO: 1 and SEQ ID NO: 2. Preferred compositions according to this aspect of the invention comprise one or more primer nucleic acid molecules having a nucleotide sequence selected from the group of nucleotide sequences consisting of SEQ ID NO: 3 and SEQ ID NO: 4.

The invention is also directed to a kit for diagnosis of predisposition or susceptibility to osteoporosis comprising one or more primer nucleic acid molecules for determining the genotype of an IL-6 gene, preferably comprising one or more PCR primers adapted to distinguish between risk and non-risk genotypes of an IL-6 gene. The invention is also directed to an apparatus for correlating IL-6 genotype with risk of predisposition or susceptibility to osteoporosis.

The invention is further directed to a method of treating an animal, preferably a human, predisposed or susceptible to osteoporosis, the method comprising (a) determining the genotype of an IL-6 gene in the animal to identify a risk genotype in the IL-6 gene; and (b) administering to the animal an effective dose of a therapeutic composition suitable to delay, reduce or prevent osteoporosis in the animal. Preferred therapeutic compositions for use in these methods comprise one or more compounds selected from the group consisting of a hormone (preferably oestrogen, testosterone or parathyroid hormone), a xanthine oxidase inhibitor, a substituted benzodiazepine, calcitonin, a bisphosphonate (preferably alendronate), sodium fluoride and calcitriol.

Other preferred embodiments of the present invention will be apparent to one of ordinary skill in light of the following description of the invention, and of the claims.

DETAILED DESCRIPTION OF THE INVENTION

The present invention is based upon the discovery of a correlation between a polymorphism in an IL-6 gene and bone mineral density; possessing a certain combination of polymorphisms, referred to above as a "risk genotype," correlates with decreased bone mineral density. A further aspect of the discovery is that the genotype is correlated with a predisposition to a osteoporosis. The invention is of advantage in that by screening for the presence of the genotype it is possible to identify individuals likely to have this genetic predisposition. According to the invention, diagnosis of predisposition or susceptibility to osteoporosis is achieved by knowledge of an individual's genotype at the IL-6 gene locus. Optionally, the assessment of an individual's risk factor is calculated by reference both to the IL-6 gene genotype and also to other known genetic or physiological or dietary or other indications. The invention in this way provides further information on which measurement of an individual's risk can be based.

A first aspect of the present invention provides a method of diagnosis of a disease in an animal, preferably a human, comprising determining the genotype of an IL-6 gene in the animal. In a second, and related aspect, the invention provides a method of identifying an animal, preferably a human, that is predisposed to or susceptible to a disease, the method comprising determining the genotype of an IL-6 gene in the animal. Typically, these methods involve determining whether the animal is homozygous or heterozygous for IL-6 gene polymorphisms. In one embodiment of the invention, the method of diagnosis comprises screening for an individual at risk of a condition or disease correlated with presence of a particular polymorphism by determining genotype at the IL-6 gene locus. In general, the methods of the invention may be useful for diagnosing, or identifying an animal predisposed or susceptible to, any disease associated with a polymorphism in an IL-6 gene, including but not limited to osteoporosis, gastrointestinal disorders (e.g., Crohn's Disease and ulcerative colitis), autoimmune and inflammatory disorders (e.g., arthritis, systemic lupus erythematosus and allergic disorders), apoptosis and the like. In particularly preferred aspects, the methods of the invention are used to diagnose, or identify an animal predisposed or susceptible to, osteoporosis.

Typically, the methods of the invention are carried out by in vitro analysis of cells or tissue samples obtained from an individual to determine the genotype of that individual at the IL-6 locus. In accordance with one suitable and conventional technique a sample of DNA-containing cells is taken from an individual (blood is one suitable source of cells) and the DNA is analysed to determine genotype of the IL-6 gene. For the purposes of this invention, blood cells include all cells of animal blood that have nuclei, ie neutrophils, eosinophils, basophils, monocytes, macrophages, granulocytes, lymphocytes and other nucleated cells. Blood cells may be obtained by any suitable technique in this art. Cells from other sources, such as tissue cells, including but not limited to epithelial cells (kidney, liver, skin, intestinal and the like), connective tissue cells (fibroblasts, adipocytes, osteocytes, osteoblasts, chondrocytes, chondroblasts and the like), nervous tissue cells (neurons, glial cells and the like) and other cell or tissue types may likewise be used in the methods of the invention, and may be obtained by any suitable technique in the art.

In one embodiment of the invention, described in detail below, the diagnosis employs amplification of fragments of an L-6 gene via polymerase chain reaction and determines whether an individual possesses a risk genotype of an IL-6 gene. As used herein, the term "risk genotype" means a genotype of an IL-6 gene that correlates with predisposition to one or more disease states, including osteoporosis. Each individual may be homozygous for one polymorphism, or heterozygous for different polymorphisms in the IL-6 gene.

In a particular embodiment of the invention, the risk genotype is located, when present, in a variable number TA tandem repeat in the 3' flank of an IL-6 gene, and the method of the invention comprises analysing the 3' flank to screen for a polymorphism therein. This analysis may be accomplished by a variety of techniques, including but not limited to amplification of a nucleic acid sequence located within the 3' flanking region of the IL-6 gene, Southern blotting of the 3' flanking region of the IL-6 gene and single strand conformational polymorphism (SSCP) mapping of the 3' flanking region of the IL-6 gene, and is most preferably accomplished by amplification of a nucleic acid sequence located within the 3' flanking region of the IL-6 gene. Preferred methods of amplification include use of the polymerase chain reaction, as described below.

The methods of the invention further optionally comprise use of a detectable label to react to the presence of one or more particular polymorphisms. Examples of suitable detectable labels that may be used according to the invention include fluorescent (e.g., fluorescein, rhodamine, phycocyanin, etc.), chemiluminescent and radioactive (e.g., $^3$H, $^{14}$C, $^{32}$P, 35S, etc.) labels. A detectable label typically induces a detectable signal upon presence of the polymorphism, and can induce a color change or a coagulation or induce a restriction site, detectable by further analytical steps. An alternative label (or indicator means) that may be used in the methods of the invention comprises one or more antibodies that have binding affinities that distinguish between respective polymorphisms.

A particular method of the invention comprises screening for a polymorphism in a TA repeat in the 3' flanking region of an IL-6 gene wherein polymorphisms are distinguished one from another by the respective sizes of the products of PCR amplification. In a preferred such method, this amplification is accomplished using one or more PCR primers adapted to amplify a nucleic acid sequence located within the 3' flanking region of an IL-6 gene, according to PCR methods that are well-known in the art (see U.S. Pat. Nos. 4,683,195; 4,683,202; and 4,800,159; see also EP 0 200 362 and EP 0 201 184). The size or sizes of the product or products obtained may then be compared with the size of reference nucleic acid molecules which may be conveniently obtained by amplifying, with the same set of PCR primers, a part of the 3' flanking region of an IL-6 gene known to contain a risk genotype. Presence of the risk genotype correlates with predisposition to osteoporosis. In a specific embodiment of the invention described in an example below, products of size about 675 bp and about 695 bp indicate a non-risk genotype of an IL-6 gene. Hence, the non-risk genotype is a heterozygous genotype in which specific polymorphic variants (or alleles) of the IL-6 gene are different on respective chromosomes. A risk genotype is (a) any homozygous IL-6 genotype or (b) a heterozygous genotype in which the PCR products are (i) not about 675 bp and (ii) not about 695 bp. For example, being heterozygous 675/695 indicates a non-risk genotype, while being homozygous 675/675 or 695/695 or heterozygous 675/non-695, non-675/695 or non-675/non-695 indicates a risk genotype.

In an embodiment of the invention, screening is carried out, for example, using PCR primers adapted to amplify a portion of the 3' flanking region, between a 5' restriction site recognized by Hind III or an isoschizomer thereof, and a 3' restriction site recognized by RsaI or an isoschizomer thereof. A non-risk genotype of this region preferably contains the sequence SEQ ID NO: 1 on one chromosome and SEQ ID NO: 2 on the other:-

```
SEQ ID NO: 1
5' ATATACACAT ATATACTATA TATACACATA
   TATATTATGT ATGTATATAT ATAGTATATA
   TAGTATATAT ACTATGTATG TATATATATA
   GTATATATAG TATATATACT ATGTATGT 3'
SEQ ID NO: 2
5' ATATACACAT ATATACTATA TATACACATA
   TATATTATGT ATGTATATAT ATAGTATATA
   TAGTATATAT ACTATGTATG TATATATATG
   TATATATAGT ATATATACTA TGTATGTATA
   TATAGTATAT ATAGTATATA TACTATGTAT
   GTGT                            3'
```

The method thus distinguishes between IL-6 genes that contain or do not contain this genotype. According to this aspect of the invention, PCR amplification is preferably carried out using one or more primers which have nucleotide sequences as set forth in SEQ ID NOs: 3 and 4:

```
SEQ ID NO: 3    5' CTTTGAGTGTGTCACGTGAAGC
SEQ ID NO: 4    5' TGCCTGGCATGTAGTAGGTGC
```

Such primer nucleic acid molecules may be produced by methods of oligonucleotide synthesis that are well-known in the art, including via organic chemical synthesis, solid state synthesis or automated synthesis. As noted above, PCR techniques are well known in the art and it would be within the ambit of a person of ordinary skill in this art to identify and produce other primers for use in the methods of the present invention that may be suitable to amplify one or more fragments of the 3' flanking region of an IL-6 gene.

The present invention also provides compositions for use in diagnosing a disease in an animal (preferably a human), or in identifying an animal (preferably a human) that is predisposed or susceptible to a disease. Diseases capable of diagnosis or identification include those listed above, most preferably osteoporosis. The diagnostic composition of a preferred embodiment of the invention is adapted to distinguish between risk and non-risk genotypes by amplification of differently sized PCR products. The products are separated by size, typically by gel electrophoresis according to conventional techniques, such that determination of whether a risk genotype is present is possible by a rapid and simple visual assessment. In another embodiment of the invention, a cell sample is analysed by flow cytometric (e.g., FACS®; Becton Dickinson, San Jose, Calif.) analysis using detectably labelled hybridization probes. The invention thus employs any suitable method for polymorphic analysis of the IL-6 gene and is not to be limited to the specific examples described.

In a specific embodiment of the invention, the diagnostic composition comprises primers having nucleotide sequences as set forth in SEQ ID NOs: 3 and 4. Using these two PCR primers, amplification of two products, one that is 675 bp in length and one that is 695 bp in length, indicates a non-risk genotype in an IL-6 gene and amplification of another product or product combination indicates a risk genotype. A risk genotype correlates with predisposition to osteoporosis.

PCR primers suitable for use in this aspect of the invention are not limited to SEQ ID NO:s 3 and 4 but instead encompass all pairs or sets of PCR primers suitable for selective amplification of the 3' flanking region of an IL-6 gene of an animal, or for amplification of that part of this region in which the polymorphism of the invention is located. Whatever primers are in fact used, indeed whatever method of analysis of the IL-6 gene is used, identification of SEQ ID NO: 1 on one chromosome and SEQ ID NO: 2 on the other indicates a non-risk genotype. Suitable alternative primers for analysis of the IL-6 gene site of interest, and methods of production thereof, will be apparent to one of ordinary skill in the art.

Thus, preferred compositions according to this aspect of the invention comprise one or more primer nucleic acid molecules adapted to amplify a portion of a 3' flanking region, particularly those capable of identifying a polymorphism in this region that is indicative of a risk genotype, of an IL-6 gene in an animal (preferably a human). Polymorphisms that may be identified using the compositions of the invention include those located within TA repeat sequences within the 3' flanking region of the IL-6 gene, including those having a nucleotide sequence corresponding to those set forth in SEQ ID NOs: 1 and 2. Particularly preferred such compositions comprise one or more primer nucleic acid molecules having a nucleic acid sequence selected from the group consisting of SEQ ID NO:3 and SEQ ID NO:4. Primer nucleic acid molecules used to form the present compositions may optionally be unlabelled or detectably labelled with one or more of the detectable labels noted above.

The compositions of the invention may also be formulated into kits for diagnosis of predisposition or susceptibility to osteoporosis in an animal, which are also provided by the invention. Kits according to the invention may comprise a carrier means, such as a box, carton or the like, having in close confinement therein one or more containers, such as bottles, tubes, vials, ampules and the like, wherein a first container contains one or more primer nucleic acid molecules for determining the genotype of an IL-6 gene in an animal which preferably are adapted to distinguish between a risk and a non-risk genotype of an IL-6 gene in the animal. Most preferably, the primer nucleic acid molecules contained in the first container of the present kits are nucleic acid molecules having a nucleotide sequence as set forth in SEQ ID NO:3 or SEQ ID NO:4.

These compositions and kits may be used in methods of identifying a risk genotype of an IL-6 gene comprising using a DNA probe adapted to hybridize under stringent hybridization conditions with a nucleic acid molecule having a nucleotide sequence as set forth in SEQ ID NO: 1 or SEQ ID NO: 2. By "stringent hybridization conditions" is intended overnight incubation at 42° C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1× SSC at about 65° C. Preferably, the probes used in this aspect of the invention comprise one or more DNA molecules complementary to substantially all or a portion of a nucleic acid molecule having a nucleotide sequence as set forth in SEQ ID NO: 1 or SEQ ID NO: 2.

In further embodiments of the invention, the diagnostic method may comprise analysis of the 3' flanking region of an IL-6 gene using the Southern blotting technique, or single strand conformational polymorphism (SSCP) mapping. Other suitable techniques for polymorphism analysis may include strand displacement amplification (SDA; U.S. Pat. No. 5,455,166), nucleic acid sequence-based amplification (NASBA; U.S. Pat. No. 5,409,818), random amplified polymorphic DNA analysis (RAPD analysis; Williams, J. G. K. et al., *Nucl. Acids Res.* 18(22):6531–6535 (1990)), arbitrarily primed PCR (AP-PCR; Welsh, J., and McClelland, M., *Nucl. Acids Res.* 18(24):7213–7218 (1990)), DNA amplification fingerprinting (DAF; Caetano-Anollés, et al., *Bio/Technology* 9:553–557 (1991)), microsatellite PCR or directed amplification of minisatellite region DNA (DAMD; Heath, D. D. et al., *Nucl. Acids Res.* 21(24):5782–5785 (1993)) and amplification fragment length polymorphism (AFLP; EP 0 534 858; Vos, P., et al., *Nucl. Acids Res.* 23(21):4407–4414 (1995)).

An additional aspect of the invention provides a diagnostic apparatus adapted to diagnose risk of predisposition or susceptibility to osteoporosis, by determining the genotype of an IL-6 gene. The diagnostic apparatus preferably comprises one or more PCR primers adapted to amplify a portion of a 3' flanking region of an IL-6 gene. The apparatus of the invention may be provided as a diagnostic kit, and may alternatively comprise one or more probes adapted to hybridize under stringent hybridization conditions with risk polymorphisms of an IL-6 gene, the probes comprising or consisting of sequences complementary to SEQ ID NO:s 1 or 2, or comprising nucleic acid molecules having a nucleic acid sequence as set forth in SEQ ID NOs:3 or 4, as described above. The apparatus may optionally include a reference indicating how results obtained using the apparatus are analysed to provide a diagnosis. A suitable reference is a chart of PCR product sizes obtained using particular PCR primers with various polymorphisms of an IL-6 gene, although other references, such as nucleic acid sizing markers or ladders, may also be used to analyse results obtained according to the invention.

The present invention is also directed to therapeutic methods. According to the invention, there is provided a method of treating an animal, preferably a human, predisposed or susceptible to a disease, the method comprising (a) determining the genotype of an IL-6 gene in the animal, as described above, to identify a risk genotype in the IL-6 gene in the animal; and (b) administering to the animal an effective dose of a pharmaceutical composition suitable to delay, reduce or prevent the disease in the animal. Thus, the goal of the present therapeutic methods is to identify individuals who are predisposed or susceptible to, but may not show any overt clinical symptoms of, a disease and, in those individuals in whom a predisposition or susceptibility is identified, treating the individuals to delay, reduce or prevent the disease. Diseases that may be treated according to the present methods include those described above, most preferably osteoporosis. Pharmaceutical compositions useful in treating such diseases will comprise one or more active components, which may vary depending upon the particular disease being treated, and a pharmaceutically acceptable carrier or excipient therefor such as those described in detail below.

One suitable treatment to prevent, reduce or delay osteoporosis, typically in women, is hormone replacement therapy which is well-known in the art. According to the invention, hormone replacement therapy using, for example, oestrogen, testosterone or parathyroid hormone, can thus be commenced in individuals likely to have a predisposition to osteoporosis but in whom osteoporosis has not yet begun to any significant extent (i.e., clinical signs of osteoporosis, obtained, for example, via bone density scanning, have not yet appeared). Another suitable treatment is use of bisphosphonates, such as xanthine oxidase inhibitors or substituted benzodiazepines, the use of which are described in U.S. Pat. Nos. 5,436,258 and 5,441,964, the contents of which are incorporated herein by reference. Still further treatments will be known to a person of skill in the art. Potential treatments are described, for example, in JP-A-09030977, WO 97/06254, JP-A-09025293, WO 97/04799, WO 97/03060 and JP-A-09012592, the contents of which are incorporated herein by reference. Currently authorised treatments for osteoporosis include the use of oestrogens, with and without progestin, the use of anabolic steroids such as nandrolone, the use of the bisphosphonate disodium etidronate, the use of salcatonin and administration of calcium supplements.

It is suspected that the use of hormone replacement therapy can carry with it a concomitant increased risk of breast cancer. The invention offers the advantage that the increased risk of breast cancer associated with hormone replacement therapy can be accepted only by those women who are known to have a likelihood of predisposition to osteoporosis.

Currently, none of the osteoporosis medications that have been approved by the Food and Drug Administration (FDA) for postmenopausal women have been approved for men. Testosterone replacement therapy may be prescribed for treatment of osteoporosis in men with low testosterone levels.

Calcitonin, a medication that slows or stops bone loss and may relieve the pain of fractures in some patients, may also be used as an active component in the pharmaceutical compositions used in the therapeutic methods of the invention. Calcitonin is approved by the FDA for the treatment of osteoporosis in postmenopausal women. While its effect in men has not been studied, evidence suggests that it may work the same in men as in women. Calcitonin is available as an injection and as a nasal spray, and its use is described in U.S. Pat. No. 5,440,012, which is incorporated herein by reference in its entirety.

Bisphosphonates, which are a class of drugs that have been shown to help preserve and increase bone density by slowing or stopping bone loss, may also be used as the active components in the pharmaceutical compositions used in the present methods. The FDA has approved a bisphosphonate known as alendronate for the treatment of postmenopausal osteoporosis in women; it is currently being studied for treatment of osteoporosis in men. There are other bisphosphonates under development.

Sodium fluoride has recently been recommended for approval by an FDA committee, and may also be used as active components in the compositions in the therapeutic methods of the invention, as may calcitriol.

Decrease in bone mineral density can also be slowed by ingested calcium supplements. Suggested levels of calcium supplementation are 1,000 mg/day for women on oestrogen replacement therapy and 1,500 mg/day for women not receiving oestrogen therapy.

According to the invention, pharmaceutical compositions comprising one or more of the therapeutic compounds described above, and a pharmaceutically acceptable carrier or excipient, may be administered to an individual predisposed to osteoporosis orally, rectally, parenterally, intrasystemically, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions used in the methods of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions used in the present methods may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drugs, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f)absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the abovementioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 μm in diameter. Suitable inert carriers include sugars such as lactose. Desirably, at least 95% by weight of the particles of the active ingredient have an effective particle size in the range of 0.01 to 10 μm.

Alternatively, the composition may be pressurized and contain a compressed gas, such as nitrogen or a liquefied gas propellant. The liquefied propellant medium and indeed the total composition is preferably such that the active ingredients do not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye. The active compounds are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the active compounds with suitable non-irritating excipients or carriers such as cocoa butter, polyethylene glycol or a suppository wax which are solid at room temperature but liquid at body temperature and therefore melt in the rectum or vaginal cavity and release the drugs.

The compositions used in the methods of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form, in addition to one or more of the active compounds described above, can contain stabilizers, preservatives, excipients and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:pp. 33 et seq (1976)).

Typical dosages and durations of treatment are as described in clinician's textbooks such as British National Formulary, incorporated herein by reference, and will be familiar to physicians and other practitioners in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Identification of Correlation Between IL-6 Genetic Polymorphism and Predisposition to Osteoporosis Patients and Methods The study was based in a regional referral centre for bone diseases in the North East of Scotland (population 0.5 million), which serves a white Caucasian population from a geographically isolated region in the UK. A cohort of 200 women were studied. Ninety one (47%) were drawn at random from the population and the remainder were consecutive referrals for clinical evaluation and bone densitometry which was performed using a Norland XR26 densitometer as previously described Br J Rheum 1995; 34:620–624. Adjusted bone density values were calculated from the raw data by multiple linear regression analysis as previously described (*Br. Med. J* 310:1357–1360 (1995); *Clin. Endocrinol.* 41:747–755 (1995)) to compensate for environmental and anthropomorphic influences on bone mass including: weight, height, age, menopausal age, smoking, HRT therapy and duration of HRT use and dietary calcium intake (by food frequency questionnaire). BMD values were also expressed as the T-score (which related measured BMD to the expected values in young healthy controls and Z-score (which relates BMD to age matched controls (*J. Bone Miner. Res.* 9:1137–1141 (1994)). Individuals with secondary causes of osteoporosis (corticosteroid use, pituitary disease, immobilisation, primary hyperparathyroidism, neoplasia, thyrotoxicosis) were excluded. The age range of the study group was 45–88 years, with a mean (+sem) age of 59.8+0.71 years. Twenty six (13.6%) were premenopausal and the remainder postmenopausal, menopause being defined as the absence of menstruation for 6 months. In the post-menopausal patients, the range of years elapsed since menopause varied from 1–38 years with a mean of 13.3+0.77 years. According to World Health Organisation (WHO) definition, 22.5% of the study group were normal, 30.5% were osteopaenic; and 47% were osteoporotic osteoporosis. These proportions are expected in a predominantly postmenopausal cohort of women, since the prevalence of osteoporosis increases with age. Fifty five individuals (27.5%) had vertebral compression fractures, diagnosed clinically and by the presence of one or more wedge or biconcave vertebral deformities on spinal radiographs. We studied a variable number tandem repeat (VNTR) polymorphism originally described by Bowcock et al (*Nucl. Acids Res.* 17:6855–6864 (1989)) situated in the 3' flank of the IL-6 gene on genomic DNA extracted from peripheral blood. The polymorphism was typed by PCR using 0.1 ng genomic DNA as template in each reaction. The following primers were used in the PCR reaction (both are shown 5'-3'): GCAACTTTGAGTGTGT-CACG (forward) (SEQ ID NO:5) and TGACGTGATGGAT-GCAAACAC (reverse) (SEQ ID NO:6). PCR was performed using Taq DNA polymerase (Boehringer Mannheim) using an Omnigene Thermal cycler (Hybaid, UK) programmed for 35 cycles of 94° c., 1 min; 60° c., 1 min; and 72° c., 1.5 min. Amplification products were separated by 5–7% polyacrylamide gel electrophoresis (PAGE) and detected by ethidium bromide staining.

Results

Analysis of genotypes in the 200 individuals studied showed evidence of 6 length variants with product sizes ranging (approximately) between 675 bp–810 bp. This finding contrasts with the previous report where only 4 variants were recognised, ranging between 610 bp–760 bp (Table 1).

TABLE 1

IL-6 VNTR Fragment Lengths[1]

| Allele | Bowcock | Allele | Present Invention |
|---|---|---|---|
| B1 | 760 bp | A | 810 bp |
| B2 | 680 bp | B | 710 bp |
| B3 | 640 bp | C | 695 bp |
|  |  | D | 690 bp |
|  |  | E | 685 bp |
| B4 | 610 bp | F | 675 bp |

[1]The fragment lengths were calculated by comparing band migration with markers of known molecular size ($\phi$X174/HaeIII digest and pSV$\beta$Gal/RsaI digest).

These differences are almost certainly attributable to the different detection methods used since PAGE electrophoresis as used here is more sensitive that the agarose gel electrophoresis in detecting small length variations. In order to investigate this discrepancy further, DNA sequencing of the products was carried out but this confirmed that the polymorphism we had detected was indeed the TA rich repeat described by Bowcock. As shown in Table 2, sequencing of our products showed data almost identical to that of the previously published sequence however, confirming that the region detected was the same.

TABLE 2

IL-6 VNTR fragment sequencing data

| | |
|---|---|
| Present Invention | ATATATACTATATAATACATATATACACTATATATAATACA (SEQ ID NO:7) |
| Bowcock | ATATATACTATATAATACATATATACACTATATATAATACA (SEQ ID NO:8) |

These results, coupled with studies on allele distribution (see below) suggest that the B1,B2, B3 and B4 alleles reported by Bowcock probably correspond to the A, B, C and F variants reported here. The limited resolution of agarose gel electrophoresis used by Bowcock would, however, have been insufficiently sensitive to detect the difference between C and D alleles, D and E alleles or E and F alleles, thus explaining why these additional alleles were missed on the original report.

In agreement with Bowcock, however, we found that most individuals in our population had one of two polymorphism: F/F (corresponding to Bowcock's B4/B4 genotype) and C/F (corresponding to Bowcock's B3/B4 genotype). Overall, 8 of the 21 possible genotypes were found, with the majority of patients falling into one of the above two categories (Table 3).

TABLE 3

IL-6 Allele Distribution

| Allele Frequency | Bowcock (56 Chromosomes) | Present Invention (400 Chromosomes) |
|---|---|---|
| B1/A | 5% | 0.75% |
| B2/B | 0 | 0.25% |
| B3/C | 11% | 19.5% |
| D | N/A[1] | 2.25% |
| E | N/A | 0.25% |
| B4/F | 84% | 77.7% |

[1]N/A: not applicable.

As shown in Table 4, analysis of IL-6 genotype in relation to bone mineral density showed a highly significant difference between spine BMD values in the C/F genotype (n=54) compared with those in the F/F genotype (n=117).

TABLE 4

Relationship between IL-6 genotype and Bone Density

| Genotype | BMD spine | BMD hip | Z-score Spine | Z-score Hip |
|---|---|---|---|---|
| C/C (n = 9) | 0.68 ± 0.10[1] | 0.49 ± 0.09 | −1.05 ± 0.45[1] | −0.94 ± 0.37 |
| A/F (n = 3) | 0.87 ± 0.13[1] | 0.64 ± 0.13 | −0.64 ± 0.33 | −0.64 ± 0.20 |
| B/F (n = 1) | 0.87 | 0.64 | −0.25 | +0.02 |
| C/E (n = 6) | 0.77 ± 0.10 | 0.64 ± 0.10 | −1.13 ± 0.39 | 0.28 ± 0.37 |
| C/F (n = 54) | 0.94 ± 0.04[2] | 0.69 ± 0.03 | −0.05 ± 0.18[2] | −0.32 ± 0.14 |
| D/F (n = 9) | 0.74 ± 0.11 | 0.53 ± 0.07 | −0.89 ± 0.55 | 0.82 ± 0.23 |
| E/F (n = 1) | 0.59 | 0.39 | +0.03 | −0.56 |
| F/F (n = 117) | 0.81 ± 0.02 | 0.61 ± 0.02 | −0.60 ± 0.11 | −0.55 ± 0.10 |

Values are mean ± SEM.
[1]$p < 0.05$ C/C vs C/F groups
[2]$p < 0.02$ C/F vs F/F groups This difference was statistically significant when bone density was expressed as the Z-score (−0.05±0.18 vs −0.60±0.1 1; p=0.011) and when adjusted BMD values were calculated to correct for confounding environmental and anthropomorphic variables such as age, menopausal age weight, height, smoking, calcium intake and HRT use by multiple linear regression analysis (0.94±0.04 vs 0.81±0.02; p=0.012). Although bone density was also higher in the C/F genotype as compared with the other genotypes studied, the difference failed to reach statistical significance because of the small numbers. Examination of environmental and anthropomorphic variables individually in relation to genotype showed no difference between the groups (data not shown) with the exception of weight which was slightly but not significantly higher in the C/F as compared with F/F genotypes (64.7+2.2 Kg vs 61.6+1.3 Kg; p=0.17).

Th present results thus indicate the existence of a correlation between a polymorphic TA repeat in the 3' flank of the IL-6 gene and bone mineral density. Specifically, after correction for confounding environmental and anthropomorphic variables, individuals of the C/F genotype had BMD values significantly higher than those of the F/F genotype. This association was highly significant at the spine and a similar effect was noted at the hip. Although BMD values of the C/F genotype also tended to be higher than all other genotypes studied here, the difference was not statistically significant due to the small numbers of rare genotypes. The mechanism of this association is unclear, since the polymorphism is in an apparently non-functional part of the IL-6 gene. Nonetheless VNTR repeats have been associated with variations in gene expression in other parts of the genome and it is possible that the TA polymorphism defined here may have some effect on IL-6 mRNA expression. Although the differences in with BMD between genotypes may be partly explained by the higher weight of individuals with the C/F genotype, difference was not statistically significant and in any case could only partly explain the difference in BMD since this persisted after correction for confounding environmental variables and anthropomorphic variables including weight.

In summary, the invention lies in use of a strong association between polymorphic variants in the 3' flank of the IL-6 gene and BMD, suggesting that genotyping at this site has clinical value in identifying patients at risk of osteoporosis. The individuals of the C/F genotype had higher BMD values than all other genotypes defined here which is relevant in identifying a subgroup of individuals who are relatively protected against developing osteoporosis.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of identifying an animal predisposed or susceptible to osteoporosis, said method comprising determining the presence of a C/F genotype or an F/F genotype in the 3' flanking region of an IL-6 gene in said animal, wherein said C/F genotype is correlated with decreased risk of osteoporosis and the F/F genotype is correlated with increased risk of osteoporosis, and wherein when said 3' flanking region of an IL-6 gene is amplified by PCR using nucleic acid primers having the nucleotide sequences as set forth in SEQ ID NO:1 and SEQ ID NO:2, said C/F genotype is indicated by obtaining DNA amplimers of sizes 695 bp and 675 bp and said F/F genotype is indicated by obtaining a DNA amplimer of size 675 bp.

2. The method of claim 1, wherein said animal is a human.

3. A method of treating an animal predisposed or susceptible to osteoporosis, said method comprising:
   (a) determining the presence of an F/F genotype in the 3' flanking region of an IL-6 gene in said animal wherein said F/F genotype is correlated with increased risk of osteoporosis, and wherein when said 3' flanking region of an IL-6 gene is amplified by PCR using nucleic acid primers having the nucleotide sequences as set forth in SEQ ID NO: 1 and SEQ ID NO:2, said F/F genotype is indicated by obtaining a DNA amplimer of size 675 bp; and
   (b) administering to said animal an effective dose of a therapeutic composition suitable to delay, reduce or prevent osteoporosis in said animal.

4. The method of claim 3, wherein said therapeutic composition comprises a compound selected from the group consisting of a hormone, a xanthine oxidase inhibitor, a substituted benzodiazepine, calcitonin, a bisphosphonate, sodium fluoride and calcitriol.

5. The method of claim 4, wherein said hormone is oestrogen, test testosterone on parathyroid hormone.

6. The method of claim 4, wherein said bisphosphonate is alendronate.

7. The method of claim 3, wherein said animal is human.

8. A method of determining or predisposition to osteoporosis in a human, said method comprising determining the presence of a C/F genotype or an F/F genotype in the 3' flanking region of an IL-6 gene in said human, wherein said C/F genotype is correlated with decreased risk of osteoporosis and the F/F genotype is correlated with increased risk of osteoporosis, and wherein when said 3' flanking region of an IL-6 gene is amplified by PCR using nucleic acid primers having nucleotide sequences as set forth in SEQ ID NO:1 and SEQ ID NO:2, said C/F genotype is indicated by obtaining DNA amplimers of sizes 695 bp and 675 bp and said F/F genotype is indicated by obtaining a DNA amplimer of size 675 bp.

9. A method of predicting an increased or decreased bone mineral density (BMD) in a human, said method comprising determining the presence of either a C/F or an F/F genotype in the 3' flanking region of an IL-6 gene in said human, wherein said C/F genotype is correlated with increased BMD and said F/F genotype is correlated with decreased BMD, and wherein when said 3' flanking region of an IL-6 gene is amplified by PCR using nucleic acid primers having nucleotide sequences as set forth in SEQ ID NO:1 and SEQ ID NO:2, said C/F genotype is indicated by obtaining DNA amplimers of sizes 695 bp and 675 bp and said F/F genotype is indicated by obtaining a DNA amplimer of size 675 bp.

10. A method of treating a human predisposed or susceptible to osteoporosis, said method comprising:
   a) determining the presence of either a C/F or an F/F genotype in the 3' flanking region of an IL-6 gene in a human, wherein said C/F genotype is correlated with decreased risk of osteoporosis and said F/F genotype is correlated with increased risk of osteoporosis and wherein when said 3' flanking region of an IL-6 gene is amplified by PCR using nucleic acid primers having nucleotide sequences as set forth in SEQ ID NO:1 and SEQ ID NO:2, a C/F genotype is indicated by obtaining DNA amplimers of sizes 695 bp and 675 bp and an F/F genotype is indicated by obtaining a DNA amplimer of size 675 bp; and
   b) administering to said human an effective dose of a therapeutic composition suitable to delay, reduce or prevent osteoporosis in said human.

11. The method of claim 3, wherein said therapeutic composition comprises a compound selected from the group consisting of a hormone, a xanthine oxidase inhibitor, a substituted benzodiazepine, calcitonin, a bisphosphonate, sodium fluoride and calcitriol.

12. The method of claim 4, wherein said hormone is oestrogen, testosterone or parathyroid hormone.

13. The method of claim 4, wherein said bisphosphonate is alendronate.

* * * * *

```
                         SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
             (A) LENGTH: 118 base pairs
             (B) TYPE: nucleic acid
             (C) STRANDEDNESS: both
             (D) TOPOLOGY: both (ii) MOLECULE TYPE: DNA (genomic)

(xi) SEQUENCE DESCRIPTION: SEQ ID NO:1:

ATATACACAT ATATACTATA TATACACATA TATATTATGT ATGTATATAT ATAGTATATA        60

TAGTATATAT ACTATGTATG TATATATATA GTATATATAG TATATATACT ATGTATGT        118

(2) INFORMATION FOR SEQ ID NO:2:

(i) SEQUENCE CHARACTERISTICS:
             (A) LENGTH: 154 base pairs
             (B) TYPE: nucleic acid
             (C) STRANDEDNESS: both
             (D) TOPOLOGY: both (ii) MOLECULE TYPE: DNA (genomic)

(xi) SEQUENCE DESCRIPTION: SEQ ID NO:2:

ATATACACAT ATATACTATA TATACACATA TATATTATGT ATGTATATAT ATAGTATATA        60

TAGTATATAT ACTATGTATG TATATATATG TATATATAGT ATATATACTA TGTATGTATA       120

TATAGTATAT ATAGTATATA TACTATGTAT GTGT                                   154

(2) INFORMATION FOR SEQ ID NO:3:

(i) SEQUENCE CHARACTERISTICS:
             (A) LENGTH: 22 base pairs
             (B) TYPE: nucleic acid
             (C) STRANDEDNESS: single
             (D) TOPOLOGY: both (ii) MOLECULE TYPE: cDNA (xi) SEQUENCE DESCRIPTION: SEQ ID NO:3:

CTTTGAGTGT GTCACGTGAA GC                                                 22
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: both (ii) MOLECULE TYPE: cDNA (xi) SEQUENCE DESCRIPTION: SEQ ID NO:4:

```
TGCCTGGCAT GTAGTAGGTG C                                       21
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: both (ii) MOLECULE TYPE: cDNA (xi) SEQUENCE DESCRIPTION: SEQ ID NO:5:

```
GCAACTTTGA GTGTGTCACG                                         20
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: both (ii) MOLECULE TYPE: cDNA (xi) SEQUENCE DESCRIPTION: SEQ ID NO:6:

```
TGACGTGATG GATGCAACAC                                         20
```

(2) INFORMATION FOR SEQ ID NO:7:

(i) SEQUENCE CHARACTERISTICS:
        (A) LENGTH: 41 base pairs
        (B) TYPE: nucleic acid
        (C) STRANDEDNESS: single
        (D) TOPOLOGY: both (ii) MOLECULE TYPE: cDNA (xi) SEQUENCE DESCRIPTION: SEQ ID NO:7:

```
ATATATACTA TATAATACAT ATATACACTA TATATAATAC A                 41
```

(2) INFORMATION FOR SEQ ID NO:8:

(i) SEQUENCE CHARACTERISTICS:
        (A) LENGTH: 41 base pairs
        (B) TYPE: nucleic acid
        (C) STRANDEDNESS: single
        (D) TOPOLOGY: both (ii) MOLECULE TYPE: cDNA (xi) SEQUENCE DESCRIPTION: SEQ ID NO:8:

```
ATATATACTA TATAATACAT ATATACACTA TATATAATAC A                 41
```